US009132446B2

(12) United States Patent
Plans et al.

(10) Patent No.: US 9,132,446 B2
(45) Date of Patent: Sep. 15, 2015

(54) MEDICAL DEVICE COATING APPARATUS AND METHODS OF USE

(71) Applicant: Abbott Laboratories, Abbot Park, IL (US)

(72) Inventors: Isaac Plans, Galway (IE); David O'Neill, Galway (IE); Matthew Coates, Boston, MA (US); Javier P. Moreno, Galway (IE)

(73) Assignee: ABBOTT LABORATORIES, Abbott Park, IL (US)

( * ) Notice: Subject to any disclaimer, the term of this patent is extended or adjusted under 35 U.S.C. 154(b) by 44 days.

(21) Appl. No.: 13/739,791

(22) Filed: Jan. 11, 2013

(65) Prior Publication Data

US 2013/0122183 A1 May 16, 2013

Related U.S. Application Data

(62) Division of application No. 11/959,325, filed on Dec. 18, 2007, now abandoned.

(51) Int. Cl.

*A61L 33/00* (2006.01)
*B05D 1/02* (2006.01)
*B05B 7/08* (2006.01)
*B05B 13/04* (2006.01)
*B05B 15/08* (2006.01)
*B05B 13/02* (2006.01)
*B05B 15/02* (2006.01)

(52) U.S. Cl.

CPC ................ *B05D 1/02* (2013.01); *B05B 7/0807* (2013.01); *B05B 13/0442* (2013.01); *B05B 15/08* (2013.01); *B05B 13/0228* (2013.01); *B05B 15/025* (2013.01)

(58) Field of Classification Search

USPC ......... 428/35.7; 427/154; 424/423; 623/1.15, 623/901; 34/282

See application file for complete search history.

(56) References Cited

U.S. PATENT DOCUMENTS 3,416,350 A 12/1968 Eagleson et al.
6,132,809 A 10/2000 Hynes et al.

(Continued)

FOREIGN PATENT DOCUMENTS

WO WO 01/91918 12/2001
WO WO 2004/012784 2/2004

(Continued)

OTHER PUBLICATIONS

Sonotek, Micromist Ultrasonic Nozzles, 2012,http://www.sono-tek.com/industrial/page/micromist.*

(Continued)

*Primary Examiner* — Dah-Wei D Yuan
*Assistant Examiner* — Andrew Bowman
(74) *Attorney, Agent, or Firm* — Workman Nydegger; Ron Devore

(57) ABSTRACT

Apparatus and methods are configured to coat a medical device, such as a stent, with a beneficial medicinal agent using one or more liquid feeds and one or more micromist nozzles. In one implementation, an agent coating rig includes a vertical adjustment means, a rotation means, and a traverse adjustment means for moving a medical device along virtually any point on an x or y axis. In additional or alternative implementations, the agent coating rig can further include a secondary horizontal adjustment means that allows adjustment along virtually any point on a z axis. Furthermore, methods and apparatus are provided for distributing the beneficial agent on the medical device, including delivering the beneficial agent efficiently over time.

17 Claims, 6 Drawing Sheets

| | |
|---|---|
| Rotation Speed | > 120 RPM |
| Flow Rate | > 100 µl / min. |
| Traveling Speed | > 0.5 mm / sec |
| Distance x | > 20 mm |
| Air Pressure | > 20 PSI |

(56) References Cited

U.S. PATENT DOCUMENTS

| | | | | |
|---|---|---|---|---|
| 7,258,891 | B2 * | 8/2007 | Pacetti et al. | 427/2.24 |
| 2001/0037694 | A1 | 11/2001 | Freifeld | |
| 2002/0132038 | A1 | 9/2002 | Birmingham | |
| 2007/0196423 | A1 * | 8/2007 | Ruane et al. | 424/423 |
| 2007/0281117 | A1 * | 12/2007 | Kaplan et al. | 428/35.7 |
| 2008/0307668 | A1 * | 12/2008 | Watterodt et al. | 34/282 |
| 2009/0155449 | A1 | 6/2009 | Plans et al. | |

FOREIGN PATENT DOCUMENTS

| | | |
|---|---|---|
| WO | WO 2007/143609 | 12/2007 |
| WO | WO 2009/079097 | 6/2009 |

OTHER PUBLICATIONS

Sono-Tek Mounting Option, Sono-Tek Corp. Mar. 13, 2012; http://www.sono-tek.com/mounting-option/.

Sono-Tek Calculating Median Drop Diameter by Nozzle Frequency, Drop Size and Distribution, Mar. 13, 2012; http://www.sono.tek.com/drop-size-and-distribution/.

U.S. Appl. No. 11/959,325, Nov. 23, 2010, Restriction Requirement.

U.S. Appl. No. 11/959,325, Mar. 17, 2011, Office Action.

U.S. Appl. No. 11/959,325, Sep. 15, 2011, Office Action.

U.S. Appl. No. 11/959,325, Mar. 29, 2012, Office Action.

U.S. Appl. No. 11/959,325, Oct. 11, 2012, Office Action.

* cited by examiner

| | |
|---|---|
| Rotation Speed | > 120 RPM |
| Flow Rate | > 100 µl / min. |
| Traveling Speed | > 0.5 mm / sec |
| Distance x | > 20 mm |
| Air Pressure | > 20 PSI |

MEDICAL DEVICE COATING APPARATUS AND METHODS OF USE

CROSS-REFERENCE TO RELATED APPLICATIONS

The present invention is a divisional of U.S. patent application Ser. No. 11/959,325, filed Dec. 18, 2007, the entirety of which is incorporated herein by reference.

BACKGROUND OF THE INVENTION

1. The Field of the Invention

The present invention relates to systems, methods, and apparatus for coating medical devices with beneficial agents, such as medicinal agents including immuno-neutral chemicals.

2. Background and Relevant Art

In the medical fields, there are a number of devices that may be used inside a patient, whether on a temporary or permanent basis. For example, a medical practitioner may use various instruments or implants for various internal operating procedures, as well as instruments used to introduce other instruments or implants inside a patient. One common medical implant used in internal operations is a stent, which may be placed inside a patient's blood vessel.

In general, the various devices or objects that are inserted or implanted within a patient's body, whether on a temporary or permanent basis, often need to be coated with one or more beneficial agents. For example, the practitioner may desire for an implant to be coated with one or more chemicals configured to release a beneficial agent over time. In other cases, the practitioner may desire the implant to be coated with one or more immuno-neutral chemicals to ensure that the body does not reject the implant or instrument for some determined period.

There are a number of different devices or assemblies that can be used to coat a medical device or apparatus, such as a stent, with a beneficial agent (or, simply "agent.") Some apparatus and techniques, such as those described in U.S. Pat. No. 5,464,650, involve applying an agent to a medical device using one or more agent coating rigs and corresponding sprayers (micromist devices). The spray apparatus used are generally configured to provide a "micromist." Creating the micromist generally involves receiving the beneficial agent (such as dissolved within a polymeric compound) and applying air and/or ultrasonic forces to the agent. The air and/or ultrasonic forces, in turn, atomize (create particles of) the agent into the mist.

In conventional operation, therefore, a technician might position the medical device of interest in a micromist spraying apparatus. The spray apparatus might then rotate the medical device while a micromist nozzle sprays the atomized agent in mist form. Rotating and spraying the medical device in this manner is generally thought to distribute the agent on the medical device fairly evenly.

Unfortunately, there remain a number of different problems with these types of spraying or misting apparatus when coating a medical device with a beneficial agent. For example, there is often some variability in agent distribution across the medical device, and thus corresponding variability in agent concentration from device to device. Other disadvantages include difficulties controlling and maintaining drug concentration, verifying drug distribution or drug loading on any given device, and varying drug distribution in a controlled and predetermined manner to effect a more desirable drug loading profile. These differences in variability can be complicated by the fact that many medical devices have a varied surface area along their length.

In general, the problems with variability in spray distribution can be due to a wide range of factors in the construction of the conventional spray apparatus, as well as in the actual spray. For example, conventional spray apparatus are typically configured to hold one specific type of micromist nozzle, which usually means that a holding portion (nozzle adaptor) of the spray apparatus is configured for a specific dimension, thereby limiting the opportunity to vary the spray characteristics through changing the micromist nozzle. If there is a different, preferred micromist nozzle with a better distribution, the technician may be required to replace the entire spray/coating rig. While a technician can sometimes position a different micromist nozzle (having a similar dimensions) into the micromist nozzle adaptor, conventional apparatus are not configured to accommodate the different micromist nozzle's delivery parameters. For example, while conventional spray apparatus are configured to move the medical device horizontally with respect to the micromist nozzle's nozzle, conventional spray apparatus usually provide no vertical variability, which could be useful to accommodate differences between micromist nozzles.

Positioning of micromist nozzles and micromist nozzle types, however, is only one aspect of conventional spray apparatus that can cause agent distribution variability. Other aspects that can negatively affect agent distribution deal with the time needed to apply the agent. For example, conventional spray apparatus are usually optimized for delivering agent at about 2 to 10 psi of pressure. At this spray pressure, it usually takes a number of repeat passes before a medical device is sufficiently covered with the agent of interest.

The more passes that are needed to coat each medical device, however, the more likely there will be downtime to remove agent build up in the liquid feed nozzles and/or micromist nozzles. In particular, longer than necessary rates of use, or more frequent than necessary numbers of passes, per medical device can mean that a technician may need to clean the micromist nozzles more frequently than necessary. Despite the obvious disadvantages of associated downtime, buildup of agent in a liquid feed nozzle and/or micromist nozzle can also vary the evenness by which the technician is able to coat a medical device with beneficial agent.

Accordingly, there are a number of disadvantages with current micromist/spray rigs and apparatus in the art that can be addressed.

BRIEF SUMMARY OF THE INVENTION

Implementations of the present invention solve one or more problems in the art with systems, methods, and apparatus configured to efficiently distribute a beneficial agent on a medical device. In one implementation, for example, an agent coating rig can be configured with one or more vertically adjustable stands, which are customizable for alternating, holding, and accommodating different types of micromist nozzles. In addition, the agent coating rig can be configured with a plurality of motors, at least one of which is used to move a medical device in a horizontal direction, and at least another of which is used to spin the medical device during agent application.

Implementations of the present invention can also include methods and apparatus for adjusting micromist nozzle pressures, and/or for using multiple micromist nozzles to enable coating a device in a single pass. Furthermore, implementations of the present invention can include methods and apparatus for cleaning the micromist nozzle(s) with efficiency, and without requiring significant down-time. Thus, the vertical adjustment mechanisms, replaceable micromist nozzle adaptors, plurality of carriage motors, and methods for spraying or cleaning the coating rig/apparatus in a single pass ensure that a medical device can be coated adequately and efficiently, with minimal downtime.

For example, an agent coating rig configured in accordance with an implementation of the present invention can include a base, as well as a vertical adjustment means positioned on the base, where the vertical adjustment means is configured to hold one or more micromist nozzles. The agent coating rig can also include rotation means configured to rotate one or more medical devices with respect to the one or more micromist nozzles, as well as traverse adjustment means positioned on the base. In at least one implementation, the traverse adjustment means and the vertical adjustment means are configured to move the one or more micromist nozzles in a corresponding x axis or y axis direction relative to the base.

In addition, a system configured in accordance with an implementation of the present invention configured to coat a beneficial agent on one or more medical devices in a single pass can include a base, as well as a vertical member slidably coupled to the base. In one implementation, the vertical member is detachably coupled to one or more micromist nozzle adaptors having corresponding one or more micromist nozzles inserted therein. The system can also include first and second threaded members configured to rotate a medical device relative to the one or more micromist nozzles. In at least one implementation, at least one of the first and second threaded members is coupled to a first motor. In addition, the system can include a traverse adjustment means coupled to a second motor.

By contrast, a method of coating a medical device with a beneficial agent in a single pass can involve receiving a medical device in a rotation means of an agent coating rig. The method can also include receiving a micromist nozzle about the medical device, as well as receiving a first liquid feed line about the micromist nozzle. In addition, the method can include rotating the medical device in the rotation means, and adjusting a y coordinate of the micromist nozzle and an x coordinate of the medical device. Furthermore, the method can include providing a beneficial agent through the first liquid feed line, where the beneficial agent is atomized upon encountering air from the micromist nozzle.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

The present invention extends to systems, methods, and apparatus configured to efficiently distribute a beneficial agent on a medical device. In one implementation, for example, an agent coating rig can be configured with one or more vertically adjustable stands, which are customizable for alternating, holding, and accommodating different types of micromist nozzles. In addition, the agent coating rig can be configured with a plurality of motors, at least one of which is used to move a medical device in a horizontal direction, and at least another of which is used to spin the medical device during agent application.

Implementations of the present invention can also include methods and apparatus for adjusting micromist nozzle pressures, and/or for using multiple micromist nozzles to enable coating a device in a single pass. Furthermore, implementations of the present invention can include methods and apparatus for cleaning the micromist nozzle(s) with efficiency, and without requiring significant down-time. Thus, the vertical adjustment mechanisms, replaceable micromist nozzle adaptors, plurality of carriage motors, and methods for spraying or cleaning the coating rig/apparatus in a single pass ensure that a medical device can be coated adequately and efficiently, with minimal downtime.

Figure 1A:
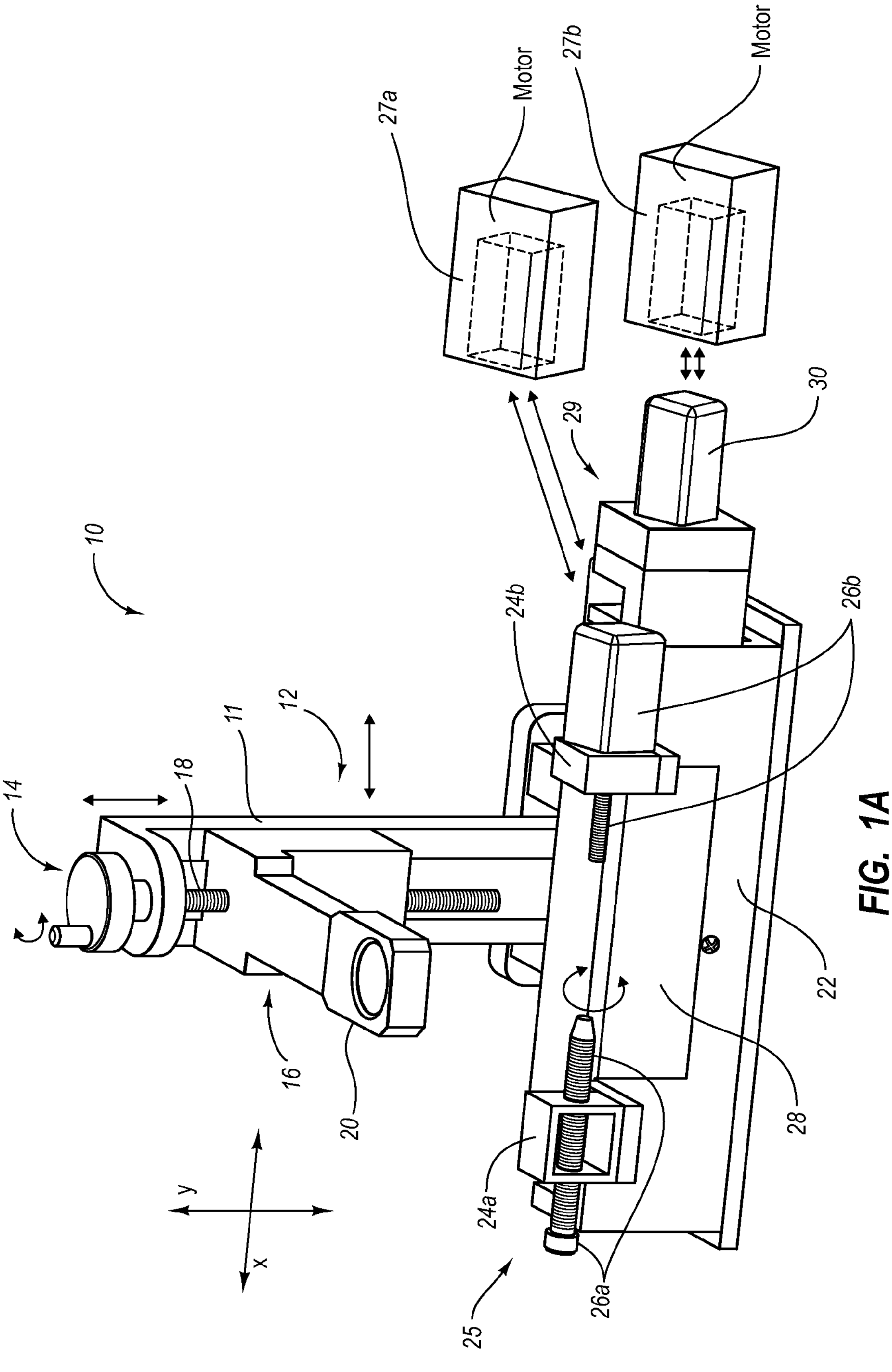
FIG. 1A illustrates a front perspective view in accordance with an implementation of the present invention of an agent coating rig with an adjustable vertical stand.
Figure 2:
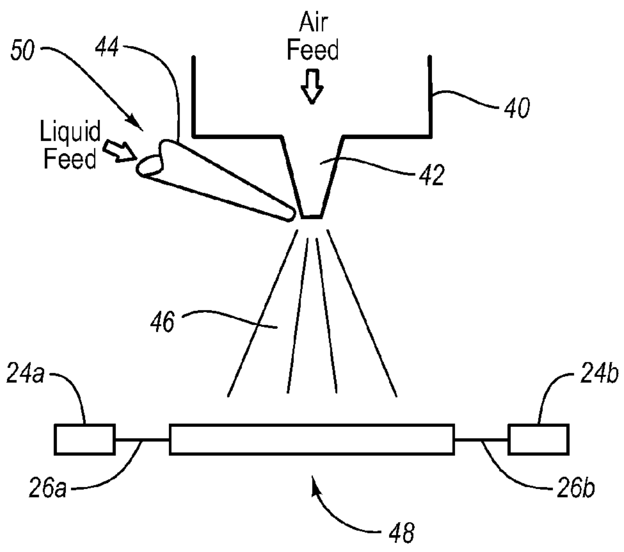
FIG. 2 illustrates a schematic diagram in accordance with an implementation of the present invention, in which a medical device is coated with one or more agents based on the illustrated parameters.

Referring now to the Figures, FIG. 1A illustrates an overview schematic diagram of an agent coating rig 10, which is configured at least in part for efficient agent distribution on a medical device (e.g., 48, FIG. 2). As referenced herein, an "agent" can comprise any substance, such as a medicinal fluid, that can be sprayed in a "mist" form when coupled with one or more micromist nozzles. In particular, the agent can include any type of medicinal fluid, such as a medicinal fluid encapsulated or otherwise dissolved within another carrier fluid. Furthermore, the agent will generally be chosen for a particular medical device on which the agent will be applied.

In any event, FIG. 1A shows that agent coating rig 10 can comprise in at least one implementation, (i) vertical adjustment means 12, (iii) rotation means 25; and (ii) traverse, or horizontal, adjustment means 29. As will be understood more fully herein, the vertical adjustment means 12, rotation means

25, and traverse, or horizontal, adjustment means 29 (hereinafter "traverse adjustment means") can be configured to operate in a concerted fashion. In particular, the vertical adjustment means 12, rotation means 25, and traverse adjustment means 29 are understood to concertedly aid a technician in applying an agent to a medical device (e.g., 48, FIG. 2) in an efficient and even manner.

For example, FIGS. 1A (and 1B) shows that vertical adjustment means 12 comprises a vertical member 11 mounted to base 22. In addition, vertical means 12 is configured, at least in part, to hold one or more micromist nozzles and further to adjust the vertical position of the micromist nozzles upward or downward relative to base 22. For example, FIG. 1A shows that vertical means 12 comprises extension 16 mounted to vertical member 11. Extension 16, in turn, is operably coupled to vertical member 11 via threaded member 18, as well as vertical control knob 14. As such, a technician can rotate vertical control knob 14 in a clockwise or counterclockwise direction to move extension 16 upward or downward relative to base 22.

The illustrated rotatable threaded member 18 and corresponding knob 14, however, are only one of the many ways for effecting vertical adjustment of a micromist nozzle (e.g., 40, FIG. 2). In other examples, extension 16 can be coupled to one or more automated means (not shown), which may or may not involve threaded member 18 and knob 14, as such. The automated means can be configured for automated vertical adjustment of extension 16 along the illustrated "y" axis.

In any case, FIG. 1A also illustrates that vertical adjustment means can include a replaceable or removable micromist nozzle adaptor 20. That is, and as also discussed in FIG. 1B, micromist nozzle adaptor 20 can be configured for detachment and reattachment. Furthermore, each of the different micromist nozzle adaptors 20 (only one is shown for convenience in FIG. 1A) can be configured with any number of internal receptacle dimensions for holding virtually any type or dimension of micromist nozzle (not shown). As such, extension 16 can be coupled with any number, type, or size of micromist nozzle adaptors 20, and corresponding micromist nozzles (not shown) having an appropriately fitted adaptor 20.

In addition, FIG. 1A shows that rotation means 25 comprises a number of different components for holding a medical device (not shown). In particular, FIG. 1A shows that rotation means 25 comprises first and second brackets 24*a* and 24*b*, which, in this case are mounted to a platform 28. Platform 28, in turn, is mounted to base 22 (via stand 23, FIG. 1B); and, as shown more fully in FIG. 1B, platform 28 is movably mounted to base 22 and traverse carriage 29. In addition, FIG. 1A shows that first and second brackets 24*a* and 24*b* are configured to receive rotatable holding members, such as threaded members 26*a* and 26*b*. As shown more fully in FIGS. 3 and 4, holding members 26*a*-*b* are configured to mount on one end directly to a medical device on which agent is to be distributed.

On another end, such as an opposing end of holding member 26*b*, the holding member 26*b* can also include one or more keys. In general, the key portion of holding member 26*b* is configured to fit within a receptacle of a motor, such as motor 27*a*. Motor 27*a*, in turn, is configured to rotate the key portion of holding member 26*b*, and thus rotate the medical device (not shown) above or about platform 28. In a similar manner, FIG. 1A further shows that traverse adjustment means 29 comprises a key 30, which, in turn, is configured to fit within a receptacle of motor 27*b*. Motor 27*b*, when coupled with key 30, can automatically rotate one or more components (not shown) to slidably reposition platform 28 (via stand 23, FIG. 1B) left and right relative base 22 and/or vertical adjustment means 12 (and/or adaptor 20).

As a preliminary matter, FIGS. 1A (and 1B) shows that agent coating rig 10 comprises two keys (26*b*, 30) having squared ends that correspondingly fit within two different squared receptacles of two different motor 27*a*-*b* apparatus. One will appreciate, however, that these illustrative distinctions are not necessarily required for operation. For example, key ends 26*b* and 30 (and corresponding receptacles) can be any number or type of shapes, such as rounded, rectangular, hexagonal, or some other random formation, so long as the shapes and corresponding motor fittings for the keys are substantially reciprocal. Furthermore, it is not necessarily required that motors 27*a* and 27*b* be separate apparatus, or mounted separately. In particular, motors 27*a*-*b* can both be mounted on a single apparatus of a separate machine, or can be mounted on the overall assembly of agent coating rig 10.

In any event, FIG. 1A shows that vertical adjustment means 12, rotation means 25, and traverse adjustment means 29 provide at least three sets of apparatus that can ensure a medical device is appropriately coated with agent. For example, a technician can adjust vertical adjustment means 12 upward or downward (in the illustrated "y" axis direction) to ensure that a given micromist nozzle is spraying agent on the medical device appropriately on a particular point of a medical device. Similarly, a technician can adjust rotation means 25 and traverse adjustment means 29 to ensure that the entire length (in the "x" direction) of a medical device is appropriately coated with agent given the position (x or y) of the vertical adjustment means 12.

Figure 1B:
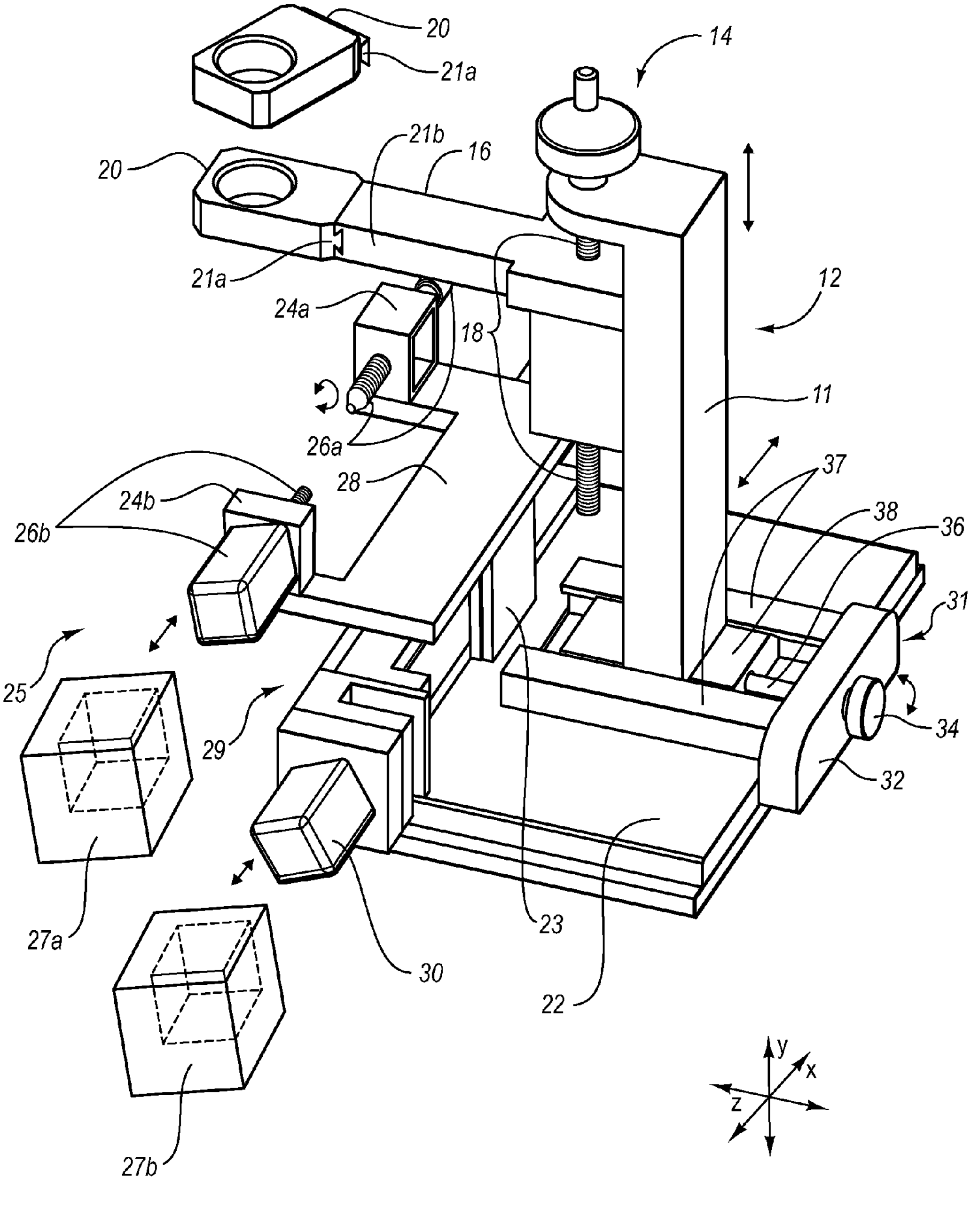
FIG. 1B illustrates a side perspective view of the agent coating rig in FIG. 1A, further showing additional details of the adjustable vertical stand relative to the agent coating rig base.

In addition to the foregoing, FIG. 1B further shows an additional set of one or more components that can be used to position vertical adjustment means 12 in an illustrated "z" axis direction. In particular, FIG. 1B illustrates a side perspective view of the agent coating rig 10 of FIG. 1A, further showing detail regarding one or more secondary horizontal adjustment means 31. In the illustrated implementation, secondary horizontal adjustment means 31 includes a carriage 32 having an internal receptacle defined at least in part by opposing walls 37. FIG. 1B further shows that the receptacle portion of carriage 32 is configured to receive base portion 38 of vertical adjustment means 12 between opposing walls 37. Base portion 38 and carriage 32 are thus optimally configured in at least one implementation to facilitate horizontal adjustment of a micromist nozzle in the illustrated "z" axis direction.

For example, FIG. 1B shows that carriage 32 of secondary horizontal adjustment means 31 also comprises a knob 34 portion for controlling threaded member 36. The knob 34, threaded member 36, and base portion 38, in turn, are configured in concert to move vertical adjustment means 12 along the axis (z) of threaded member 36. For example, in one implementation, base portion 38 comprises a reciprocally threaded receptacle, which moves in the illustrated z axis direction depending on the threaded member 36 rotation. In one implementation, a technician can rotate knob 34, and hence threaded member 36, in the clockwise direction, causing vertical adjustment means 12 (via base 38) to move in a negative z direction. By contrast, the technician can rotate knob 34, and hence threaded member 36, in a counterclockwise rotation, causing vertical adjustment means 12 (via base 38) to move in the positive z direction, or vice-versa.

One will appreciate, therefore, that secondary horizontal adjustment means 31 can provide a technician with yet another basis for adjusting the position of a micromist nozzle relative to a medical device. Of course, the illustrated mechanisms and adjustment means are only exemplary. For example, as previously explained above regarding motors 27_a-b_, vertical adjustment means 12 and secondary horizontal adjustment means 31 need not necessarily be only manually-based adjustment mechanisms, such as illustrated. In particular, knobs 14 and 34 may alternatively be configured as one or more keys (or other coupling mechanisms) to be fit into one or more different motors, whereupon adjustments are made through automated mechanisms. Thus, vertical adjustment means 12 and secondary horizontal means 31 can also operate automatically, much like as illustrated for rotation means 25 and traverse adjustment means 29.

In addition, and as previously mentioned, FIG. 1B shows that vertical extension 16 can be coupled to one or more micromist nozzle adaptors 20. In general, the one or more micromist nozzle adaptors 20 can be configured to be removable or replaceable/re-attachable with respect to extension 16. For example, FIG. 1B shows that micromist nozzle adaptor 20 can be configured with any number or style of mating components 21_a_, which, in turn, are configured to mate or couple with a reciprocally-styled component or receptacle 21_b_ of extension 16. The illustrated dovetail configuration for mating components 21_a-b_, therefore, is merely exemplary of one of the many possible coupling configurations.

In any event, one will appreciate that the remove-ability or replace-ability of micromist nozzle adaptor 20 with respect to extension 16 of vertical means 12 means that virtually any type of micromist nozzle adaptor 12 can be used with rig 10, as long as there is a match between mating components 21_a-b_. Furthermore, there is little or no complication with interchanging micromist nozzles since the coating rig 10 can be easily adjusted in any of an x, y, and z axis direction to accommodate different micromist nozzle positioning or operating variability.

The above-described coating rig 10 and related configurations, however, are only some of the means available for ensuring that an agent can be adequately and efficiently distributed on a medical device. In particular, implementations of the present invention further include methods and parameter configurations that allow a given micromist nozzle and corresponding liquid feed nozzles to distribute or coat an agent on a medical device, particularly in a single pass. Furthermore, and as discussed more fully below, implementations of the present invention provide mechanisms for easily cleaning a given liquid feed nozzle, thereby improving operating efficiency as well the distribution of agent over time.

For example, at least one way in which a device can be coated in a single pass is through the use of uncommonly high micromist nozzle pressurization (e.g., using a BINKS or SHEER nozzle). As a preliminary matter, FIG. 2 shows that the beneficial agent is provided through a liquid feed nozzle 44, which in turn is positioned adjacent a micromist nozzle 40 (and corresponding nozzle 42). When the agent exits liquid feed nozzle 44, the force of the air exiting nozzle 42 causes the agent to form a mist of "atomized" particles or droplets, which then coat the surface of the rotating medical device 48. As previously mentioned, conventional micromist nozzle pressurization is ordinarily between about 2 and about 10 pounds per square inch (psi). Pressures in this general range tend to create a distribution of agent droplets (primary atomization of the agent) that are typically about 10 μm.

Figure 3:
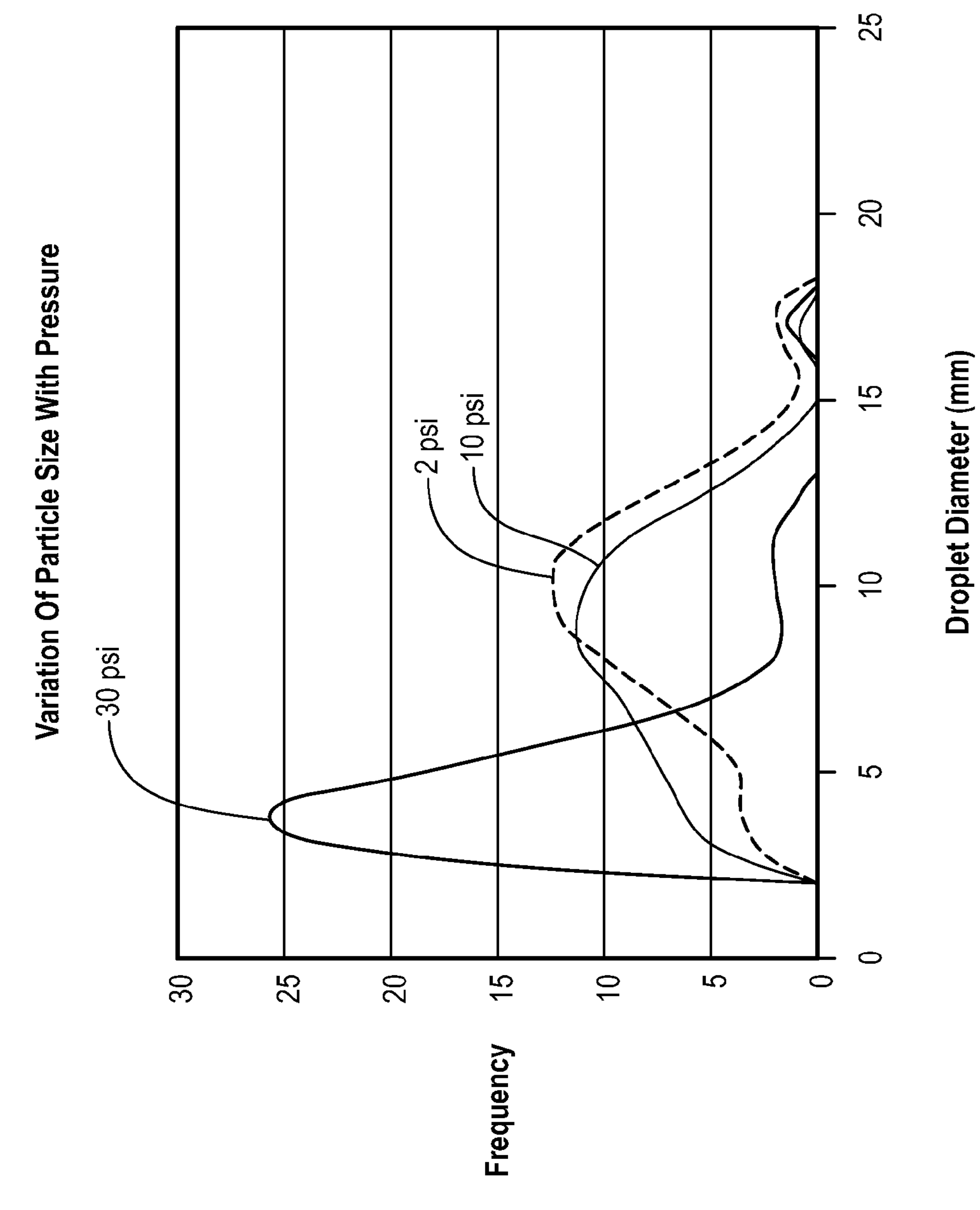
FIG. 3 is a chart illustrating the distribution of agent particle size compared with micromist nozzle pressure, in accordance with an implementation of the present invention.

Implementations of the present invention, however, include doubling, and even tripling (and beyond) these conventional pressures, which can lead to unexpected benefits, such as secondary atomization. As shown in FIG. 3, for example, increasing the air pressure through a given nozzle to as high as about 20 psi or about 30 psi, or greater, can cause secondary atomization of the agent droplets. Specifically, at pressures of about 20-30 psi or greater, the majority of agent droplets shear apart. This results in agent droplet diameters (in the resulting mist) of about 5 μm, which is about half the size of conventional droplets.

The benefits of this secondary atomization are numerous. For example, the 5 μm droplet diameter size (due to secondary atomization) can lead to reduced coating failure due to webbing effects. In addition, the 5 μm droplet diameter size can lead to improved coverage on the given medical device, as well as faster production time (i.e., coating of the medical device in coating rig 10). In one implementation of a method, therefore, the technician sets at least an air pressure parameter of a micromist nozzle (e.g., 40, FIG. 2) for at least about 20 psi. In an additional or alternative implementation of the method, the technician sets at least an air pressure parameter of about 30 psi or greater.

Referring again to FIG. 2, however, a number of other parameters can also be adjusted to quicken or improve the efficiency of production time, in addition to adjusting air pressure. In one implementation, each of these parameters can be adjusted on coating rig 10 to ensure that a medical device 48 is coated sufficiently and evenly with the agent (via mist 46) in a single pass. For example, in at least one implementation, a technician sets rotation means 25 to rotate medical device 48 at about 120 rotations per minute (rpm) or greater, and further adjusts a flow rate of the agent to about 100 μl/min or greater. The technician can also set traverse adjustment means 29 for a traverse speed of about 0.5 mm/sec. or greater. Furthermore, the technician can use vertical adjustment means 12 to position the air nozzle 42 a distance of from about 20 mm (or farther) in distance along the y axis (FIGS. 1A-1B) from the medical device 48.

Figure 4:
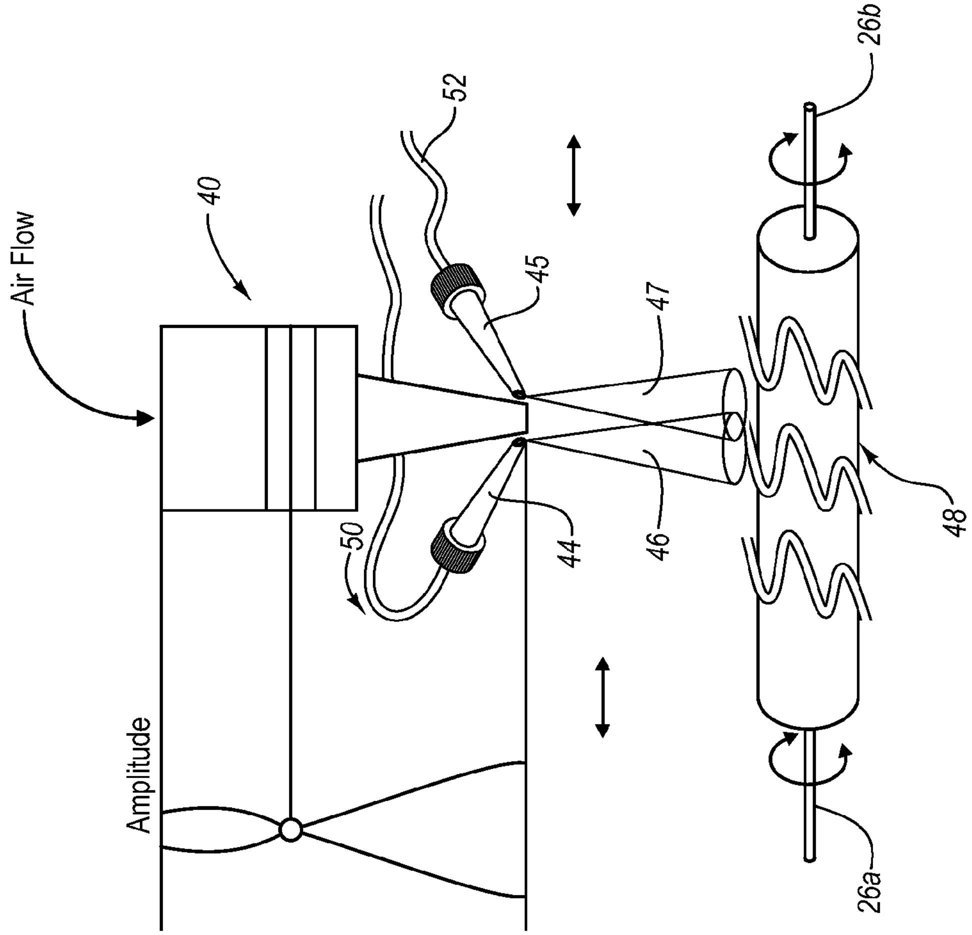
FIG. 4 illustrates a schematic diagram in accordance with an implementation of the present invention in which a plurality of liquid nozzles are used to distribute the agent.

Although the above-described parameters are geared primarily for use with higher pressure systems, implementations of the present invention can also provide "single-pass" preparations using two different liquid feed nozzles operating at lower pressures (e.g., between about 2-10 psi). For example, FIG. 4 illustrates an overview schematic diagram in which two nozzles are used to efficiently distribute a beneficial agent onto a device 48. In particular, FIG. 4 shows that a technician can use micromist nozzle 40, as before, but, in this implementation, alternatively uses two different liquid feed lines 50 and 52, which correspondingly distribute the same agent via liquid nozzles 44 and 45. As with the previous examples in FIGS. 2 and 3, the agent that is delivered from feed lines 50 and 52 through corresponding liquid feed nozzles 44 and 45 is atomized (46 and 47) when the agent is combined with air exiting micromist nozzle 40.

At least one advantage of this multiple liquid feed nozzle implementation is that similar effects to "secondary atomization" can be observed, even though operating at approximately between about 2 psi to about 10 psi. Furthermore, the benefits of secondary atomization can be achieved where high pressurization may be difficult or unavailable. Accordingly, FIGS. 3 and 4 provide additional or alternative implementations for single-pass preparations/coatings of a medical device.

Figure 5:
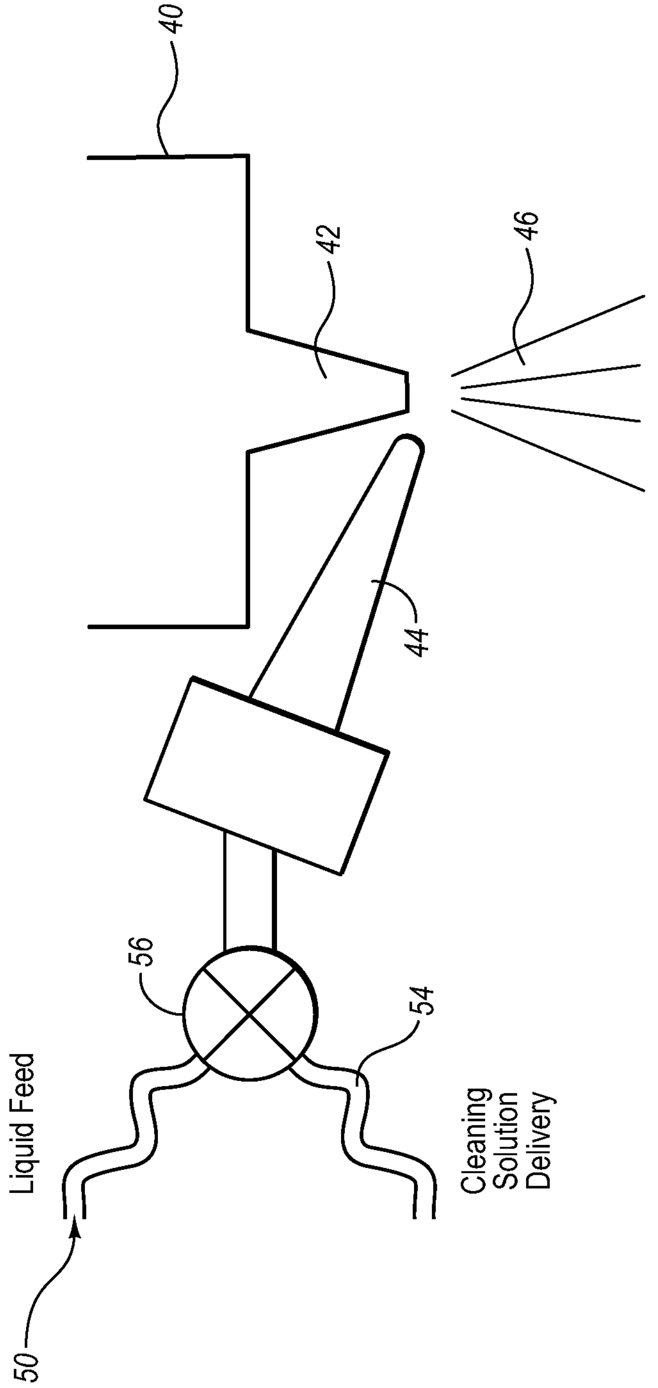
FIG. 5 illustrates a schematic diagram in accordance with an implementation of the present invention in which a nozzle for delivering agent is coupled with a plurality of liquid feeds for delivering a beneficial agent or a cleaning solution through a single nozzle.

FIG. 5 illustrates still another implementation of the present invention for enhancing the efficiency of medical device coating operations. In particular, FIG. 5 illustrates an implementation of the present invention configured for introducing a cleaning solution both to a liquid nozzle 44 and micromist nozzle 42. To this end, FIG. 5 shows that liquid feed line 50 can be communicatively coupled with a cleaning solution delivery line 54 via one or more coupling members 56. The coupling member 56 is generally configured to turn on or off a particular liquid feed line, and hence what is delivered through liquid feed nozzle 44. Thus, for example, when a technician rotates coupling member 56 into one position, coupling member 56 closes cleaning solution feed line 54, whereby only liquid agent 50 can enter into and exit out of nozzle 44. Alternatively, when a technician moves coupling member 56 into a different position, coupling member 56 closes agent liquid feed line 50, whereby only cleaning solution can enter into and exit out of nozzle 44.

Providing a cleaning solution in this manner can add a number of different benefits. In particular, providing the cleaning solution through the same nozzle 44 through which liquid agent is delivered can help increase the use time and efficiency of nozzle 44. That is, periodically delivering cleaning solution through nozzle 44 (rather than adjacent to the nozzle, as is typically done) ensures the nozzle 44 is cleaned both internally and externally, and that buildup is removed both internally and externally. Maintaining a clean, relatively build-up free nozzle 44 ensures that agent can be coated on a medical device (e.g., 48) in a much more even manner, and for a longer period than previously possible.

Accordingly, FIGS. 1A-5 provide a number of additional and/or alternative implementations of systems and apparatus configured for efficient, even, and long-lasting use of a coating rig (and related apparatus) that delivers agent evenly and efficiently onto a medical device. In particular, implementations of the present invention provide one or more agent coating rigs that are easily adaptable not only to multiple types of micromist nozzles, but also to accommodate the flow and/or pressure variability associated the multiple types of micromist nozzles. Furthermore, implementations of the present invention provide a number of different method and apparatus configurations of parameters, such as air pressure, and rotation rates, as well as of apparatus for delivering liquid agent and/or cleaning solution, which enhance the life and operation efficiency of the inventive systems and components.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A method of coating a medical device with a beneficial agent in a single pass, comprising the steps of:
- receiving a medical device in a rotation means of an agent coating rig;
- receiving a micromist nozzle about the medical device;
- receiving a first liquid feed line about the micromist nozzle;
- rotating the medical device in the rotation means;
- adjusting a y coordinate of the micromist nozzle and an x coordinate of the medical device;
- providing a beneficial agent through the first liquid feed line; and
- atomizing the beneficial agent upon encountering air from the micromist nozzle at greater than 30 psi, atomizing the beneficial agent includes creating secondary atomization with a majority of droplets of the beneficial agent being sheared apart during secondary atomization, a frequency of droplets having about 5 μm diameter being about 20 percent of the droplets and a maximum frequency of droplets below 5 μm being greater than 25 percent of the droplets.

2. The method as recited in claim 1, further comprising a step of adjusting a z coordinate of the micromist nozzle through secondary horizontal adjustment means.

3. The method as recited in claim 1, further comprising providing the beneficial agent through a second liquid feed line at the same time as the first liquid feed line, wherein the beneficial agent is atomized when exiting both of the first and second liquid feed lines upon encountering air from the micromist nozzle.

4. The method as recited in claim 1, further comprising a step of delivering a cleaning solution through first liquid feed line.

5. The method as recited in claim 1, wherein the step of creating secondary atomization comprises applying air out of the micromist nozzle at greater than 20 psi.

6. The method as recited in claim 5, further comprising the steps of:
- setting a rotation speed of the medical device at about 120 rpm or greater;
- setting a flow rate of the beneficial agent through the first liquid feed line at about 100 μl/min. or greater; and
- setting a traverse adjustment means to adjust an x coordinate for the medical device at a speed of about 0.5 mm/sec or greater.

7. A method of coating a medical device with a beneficial agent in a single pass, comprising the steps of:
- positioning a medical device in a rotation means of an agent coating rig;
- positioning a micromist nozzle adjacent the medical device at a distance of about 20 mm or greater from the medical device;
- rotating the medical device in the rotation means; and
- atomizing the beneficial agent directed toward the medical device with air from the micromist nozzle at greater than 30 psi, atomizing the beneficial agent includes creating secondary atomization with a majority of droplets of the beneficial agent being sheared apart during secondary atomization, the sheared droplets having a droplet diameter of about 5 μm, a frequency of droplets having about 5 μm diameter being about 20 percent of the droplets and a maximum frequency of droplets below 5 μm being greater than 25 percent of the droplets.

8. The method as recited in claim 7, further comprising a step of adjusting an x coordinate, a y coordinate or a z coordinate of the micromist nozzle.

9. The method as recited in claim 8, further comprising a step of adjusting an x coordinate of the medical device.

10. The method as recited in claim 7, further comprising providing the beneficial agent through a first liquid feed line and a second liquid feed line, wherein the beneficial agent is atomized when exiting both of the first and second liquid feed lines upon encountering air from the micromist nozzle.

11. The method as recited in claim 7, further comprising a step of delivering a cleaning solution through first liquid feed line.

12. The method as recited in claim 7, further comprising the steps of:
- setting a rotation speed of the medical device at about 120 rpm or greater;
- setting a flow rate of the beneficial agent through the first liquid feed line at about 100 μl/min. or greater; and
- setting a traverse adjustment means to adjust an x coordinate for the medical device at a speed of about 0.5 mm/sec or greater.

13. A method of coating a medical device with a beneficial agent in a single pass, comprising the steps of:

positioning a medical device in a rotation means of an agent coating rig;

positioning a micromist nozzle adjacent the medical device at a distance of about 20 mm or greater from the medical device;

rotating the medical device in the rotation means; and atomizing the beneficial agent directed toward the medical device with air from the micromist nozzle at about 30 psi or greater, atomizing the beneficial agent includes creating secondary atomization with a majority of droplets of the beneficial agent being sheared apart during secondary atomization and producing a final droplet size of about 5 μm, a frequency of the droplets having about 5 μm diameter being about 20 percent of the droplets, a maximum frequency of droplets below 5 μm being greater than 25 percent of the droplets, and a maximum diameter of droplets being less than 15 mm.

14. The method as recited in claim 13, further comprising a step of adjusting an x coordinate, a y coordinate or a z coordinate of the micromist nozzle.

15. The method as recited in claim 14, further comprising a step of adjusting an x coordinate of the medical device.

16. The method as recited in claim 13, further comprising a step of delivering a cleaning solution through first liquid feed line.

17. The method as recited in claim 13, further comprising the steps of:

setting a rotation speed of the medical device at about 120 rpm or greater;

setting a flow rate of the beneficial agent through the first liquid feed line at about 100 μl/min. or greater; and setting a traverse adjustment means to adjust an x coordinate for the medical device at a speed of about 0.5 mm/sec or greater.

* * * * *